(12) United States Patent
Yamazoe et al.

(10) Patent No.: US 9,059,568 B2
(45) Date of Patent: Jun. 16, 2015

(54) OPTICAL ELECTRICAL FIELD ENHANCING DEVICE AND MEASURING APPARATUS EQUIPPED WITH THE DEVICE

(71) Applicant: FUJIFILM Corporation, Tokyo (JP)

(72) Inventors: Shogo Yamazoe, Ashigarakami-gun (JP); Masayuki Naya, Ashigarakami-gun (JP); Shinya Hakuta, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/033,127

(22) Filed: Sep. 20, 2013

(65) Prior Publication Data

US 2014/0016127 A1   Jan. 16, 2014

Related U.S. Application Data

(63) Continuation of application No. PCT/JP2012/001866, filed on Mar. 16, 2012.

(30) Foreign Application Priority Data

Mar. 22, 2011 (JP) ................................. 2011-062091

(51) Int. Cl.
  *G01N 21/55* (2014.01)
  *H01S 3/30* (2006.01)
  (Continued)

(52) U.S. Cl.
  CPC . *H01S 3/30* (2013.01); *B82Y 20/00* (2013.01); *G01N 21/554* (2013.01); *G01N 21/648* (2013.01); *G01N 21/658* (2013.01)

(58) Field of Classification Search
  CPC . G01N 21/554; G01N 21/648; G01N 21/658; B82Y 20/00; H01S 3/30
  USPC ........................................................ 356/445
  See application file for complete search history.

(56) References Cited

U.S. PATENT DOCUMENTS 4,190,321 A   2/1980   Dorer et al.
7,288,419 B2   10/2007   Naya
(Continued)

FOREIGN PATENT DOCUMENTS

EP   1 445 601 A2   8/2004
EP   2 618 133 A1   7/2013
(Continued)

OTHER PUBLICATIONS

Ghadarghadr et al., "Plasmonic array nanoantennas on layered substrates: modeling and radiation characteristics", Optics Express, Oct. 12, 2009, vol. 17, No. 21, pp. 18556-18570.
(Continued)

*Primary Examiner* — Roy M Punnoose
(74) *Attorney, Agent, or Firm* — Birch, Stewart, Kolasch & Birch, LLP (57) ABSTRACT

An optical electrical field enhancing device includes: a transparent substrate having a structure of fine protrusions and recesses on the surface thereof; and a metal structure layer of fine protrusions and recesses formed on the surface of the structure of fine protrusions and recesses. The metal structure layer of fine protrusions and recesses has a structure of fine protrusions and recesses, in which the distances among adjacent protrusions are less than the distances among corresponding adjacent protrusions of the structure of fine protrusions and recesses of the transparent substrate.

12 Claims, 7 Drawing Sheets

(51) Int. Cl.
*B82Y 20/00* (2011.01)
*G01N 21/552* (2014.01)
*G01N 21/64* (2006.01)
*G01N 21/65* (2006.01)

(56) References Cited

U.S. PATENT DOCUMENTS

| | | | |
|---|---|---|---|
| 7,358,079 B2* | 4/2008 | Schurmann-Mader et al. | 435/287.1 |
| 7,678,565 B2* | 3/2010 | Schurmann-Mader et al. | 435/287.1 |
| 8,803,105 B2* | 8/2014 | Naya et al. | 250/459.1 |
| 2002/0182631 A1* | 12/2002 | Schurmann-Mader et al. | 435/6 |
| 2003/0231304 A1 | 12/2003 | Chan et al. | |
| 2004/0161369 A1 | 8/2004 | Chan et al. | |
| 2004/0183176 A1 | 9/2004 | Naya et al. | |
| 2007/0217003 A1* | 9/2007 | May et al. | 359/454 |
| 2008/0037022 A1 | 2/2008 | Nishikawa et al. | |
| 2008/0218761 A1 | 9/2008 | Nishikawa et al. | |
| 2013/0182248 A1 | 7/2013 | Naya et al. | |
| 2013/0182343 A1* | 7/2013 | Naya et al. | 359/868 |

FOREIGN PATENT DOCUMENTS

| | | |
|---|---|---|
| EP | 2 618 134 A1 | 7/2013 |
| JP | 61-48124 A | 3/1986 |
| JP | 9-202649 A | 8/1997 |
| JP | 2004-279364 A | 10/2004 |
| JP | 2006-514286 A | 4/2006 |
| JP | 2006-145230 A | 6/2006 |
| JP | 2008-8631 A | 1/2008 |
| JP | 2008-216055 A | 9/2008 |
| JP | 2009-109395 A | 5/2009 |
| JP | 2009-236830 A | 10/2009 |
| JP | 4347801 B2 | 10/2009 |
| JP | 2010-203900 A | 9/2010 |
| JP | 2012-63293 A | 3/2012 |
| JP | 2012-63294 A | 3/2012 |
| WO | WO 2005/078415 A1 | 8/2005 |

OTHER PUBLICATIONS

International Search Report, issued in PCT/JP2012/001866, dated Jul. 31, 2012.
PCT/ISA/237, issued in PCT/JP2012/001866, dated Jul. 31, 2012.
Japanese Office Action and English translation thereof, issued Jul. 8, 2014, for Japanese Application No. 2011-062091.
"Sputter Deposition", Wikipedia, Feb. 9, 2011, pp. 1-6 XP055131826, Retrieved from the Internet: URL:http://en.wikipedia.org/w/index.php? title.Sputter_deposition&oldid=413009007.
Cheng, Hui-Wen, et al., "Investigation of Raman enhancement in hydrothermally roughened SERS-active substrates", Elsevier, Computer Physics Communications, Jan. 2011, vol. 182, pp. 260-262.
Dhawan, Anuj, et al., "Fabrication of novel plasmonics-active substrates", Proc. Of SPIE, vol. 7205, Feb. 6, 2009, pp. 72050S-1-72050S-12, XP055131874.
Extended European Search Report for European Application No. 12760569.9, dated Aug. 6, 2014.
Yang, Jung-Yen, et al., "Detection of *Staphylococcus Aureus* Using Hydrothermally Roughened Substrates", IEEE 3rd International Conference on Nano/Molecular Medicine and Engineering, Tainan, Oct. 18-21, 2009, pp. 210-214.
Yang, Jung-Yen, et al., "Surface-Enhanced Raman Scattering Active Substrates", IEEE Nanotechnology Magazine, Mar. 2011, vol. 5, No. 1, pp. 12-16, XP011348529.
Foreign Office Action of Application No. 201280014387.5 dated Mar. 13, 2015.

* cited by examiner

OPTICAL ELECTRICAL FIELD ENHANCING DEVICE AND MEASURING APPARATUS EQUIPPED WITH THE DEVICE

CROSS REFERENCE TO RELATED APPLICATIONS

This application is a Bypass Continuation of PCT International Application No. PCT/JP2012/001866 filed on Mar. 16, 2012, which claims priority under 35 U.S.C §119(a) to Patent Application No. 2011-062091 filed in Japan on Mar. 22, 2011, all of which are hereby expressly incorporated by reference into the present application.

TECHNICAL FIELD

The present invention is related to an optical electrical field enhancing device equipped with a metal structure of fine protrusions and recesses capable of inducing localized plasmon, and a measuring apparatus equipped with the optical electrical field enhancing device.

BACKGROUND ART

Sensor devices that utilize the electrical field enhancing effect due to localized plasmon on the surfaces of metals and electrical field enhancing devices of Raman spectroscopic devices are known. Raman spectroscopy is a technique that obtains the spectrum of Raman scattered light (Raman spectrum) by spectrally analyzing scattered light obtained by irradiating a substance with a single wavelength light beam, and is utilized to identify substances.

There is a Raman spectroscopy technique called SERS (Surface Enhanced Raman Scattering) that utilizes an optical electrical field enhanced by localized plasmon resonance in order to amplify weak Raman scattered light (refer to S. Ghadarghadr et al., "Plasmonic array nanoantennas on layered substrates: modeling and radiation characteristics", OPTICS EXPRESS, Vol. 17, No. 21, pp. 18556-18570, 2009). SERS utilizes the principle that when light is irradiated onto a metal body, particularly a metal body having nano order protrusions and recesses on the surface thereof, while the metal body is in contact with a substance, optical electrical field enhancement occurs due to localized plasmon resonance, and the intensity of Raman scattered light of a sample in contact with the surface of the metal body is amplified. Surface enhanced Raman scattering can be executed by employing a substrate having a metal structure of protrusions and recesses on the surface thereof as a carrier (substrate) that holds test subjects.

Si substrates, on the surface of which protrusions and recesses are provided, having metal films formed on the surface having the protrusions and recesses, are mainly employed as substrates having metal structures of protrusions and recesses on the surfaces thereof (refer to PCT Japanese Publication No. 2006-514286. Japanese Patent No. 4347801, and Japanese Unexamined Patent Publication No. 2006-145230).

In addition, an Al substrate, the surface of which is anodized such that a portion thereof becomes a metal oxide layer ($Al_2O_3$) and a plurality of fine pores which are formed naturally within the metal oxide layer during the anodizing process are filled with metal, has also been proposed (refer to U.S. Pat. No. 7,288,419).

DISCLOSURE OF THE INVENTION

The conventional optical electrical field enhancing substrates disclosed in PCT Japanese Publication No. 2006-514286. Japanese Patent No. 4347801, Japanese Unexamined Patent Publication No. 2006-145230, and U.S. Pat. No. 7,288,419 are of configurations in which a structure of fine protrusions and recesses is formed on the surface of a substrate formed by an opaque material such as Si and Al, and a metal film is formed on the surface of the structure of fine protrusions and recesses or metal is embedded in the recesses. U.S. Pat. No. 7,288,419 discloses an example in which a transparent substrate such as a glass substrate is employed. However, the structure of fine protrusions and recesses itself is constituted by an opaque material such as silicon and germanium.

Conventional Raman spectroscopy apparatuses are configured to detect Raman scattered light from the side of the surface of a sample. However, in the case that cells, which are samples having sizes on the order of micrometers, are test subjects, the sample itself becomes an obstruction to Raman scattered light. Therefore, it had been difficult to receive weak Raman light at a high S/N ratio.

The present invention has been developed in view of the foregoing circumstances. It is an object of the present invention to provide an optical electrical field enhancing device capable of detecting Raman scattered light at high sensitivity, and a measuring apparatus equipped with the optical electrical field enhancing device.

An optical electrical field enhancing device of the present invention comprises:

a transparent substrate having a structure of fine protrusions and recesses on the surface thereof; and a structure layer of fine protrusions and recesses formed of metal on the structure of fine protrusions and recesses of the transparent substrate;

the metal structure layer of fine protrusions and recesses having a structure of fine protrusions and recesses in which the distances among adjacent protrusions is less than the distances among adjacent protrusions corresponding thereto in the structure of fine protrusions and recesses of the transparent substrate; and an enhanced optical electrical field being generated on the surface of the metal structure layer of fine protrusions and recesses by an optical electrical field enhancing effect of localized plasmon induced on the surface of the metal structure layer of fine protrusions and recesses by light irradiated onto the structure layer of fine protrusions and recesses.

In the case that a metal film is uniformly formed along a structure of fine protrusions and recesses of a transparent substrate, the metal structure layer of fine protrusions and recesses will have the same structure of protrusions and recesses as the structure of fine protrusions and recesses of the transparent substrate. Therefore, the distances among adjacent protrusions of the metal structure layer of protrusions and recesses will be equal to the distances among adjacent protrusions of the structure of fine protrusions and recesses of the transparent substrate. For this reason, the present invention does not include cases in which a uniform metal film is formed on the structure of fine protrusions and recesses of a transparent substrate.

Note that the distance between adjacent protrusions is defined as the distance from the peak of a lower protrusion within a pair of adjacent protrusions to a position of the other protrusion having half the depth, when viewed as across section, of the deepest portion of a recess between the adjacent protrusions. The cross section can be observed by a SEM (Scanning Electron Microscope), and the distances among protrusions can be obtained from SEM images.

In addition, it is not necessary for the distances among all adjacent protrusions of the structure of fine protrusions and recesses in the metal structure layer of fine protrusions and recesses to be less than the distances among corresponding adjacent protrusions of the structure of protrusions and recesses of the substrate. That is, the metal structure layer of fine protrusions and recesses may partially include portions at which the distances among adjacent protrusions are equal to or greater than the distances among corresponding adjacent protrusions of the structure of protrusions and recesses of the substrate.

Note that here, the metal structure layer of fine protrusions and recesses has a structure of fine protrusions and recesses capable of generating localized plasmon. Note that a structure of fine protrusions and recesses capable of generating localized plasmon is generally a structure of protrusions and recesses having an average length of protrusions at least in one of a direction perpendicular to a substrate and a direction parallel to the substrate which is less than the wavelength of an excitation light beam.

It is preferable for the optical electrical field enhancing device of the present invention to be that in which the structure of fine protrusions and recesses of the metal structure layer of fine protrusions and recesses efficiently generates an enhanced optical electrical field at a surface transparent substrate opposite the surface on which the metal structure layer of fine protrusions and recesses is formed, with respect to light irradiated from the side of the transparent substrate. Specifically, it is preferable for the thickness of the metal structure layer of fine protrusions and recesses to be 400 nm or less in the case that a gold film is formed by vapor deposition, and to be 90 nm or less in the case that a silver film is formed by vapor deposition. Here, the thickness in the case that vapor deposition is employed to form a film means that an amount of metal (gold or silver) that forms a film having a thickness of 400 nm or less or 90 nm or less on a flat substrate is used to perform vapor deposition.

It is preferable for the structure of fine protrusions and recesses of the metal structure layer of fine protrusions and recesses to include portions at which the distance among adjacent protrusions are 20 nm or less.

Note that the average length among adjacent protrusions and the average length of the protrusions in the direction perpendicular to and the direction parallel to the substrate can be obtained by imaging a cross sectional image of the structure of fine protrusions and recesses with a SEM, binarizing the image by an image process, and administering a statistical process.

In the present specification, the term transparent refers to a transmissivity of 50% or greater with respect to irradiated light and with respect to light generated by a test subject due to the irradiated light. Note that it is more preferable for the transmissivity with respect to these types of light to be 75% or greater, and even more preferably, 90% or greater.

In the optical electrical field enhancing device of the present invention, it is preferable for the structure of fine protrusions and recesses of the metal structure layer of fine protrusions and recesses to be constituted by fine particulate structures, which are formed by metal that constitutes the metal structure layer of fine protrusions and recesses agglomerating on the surface of the structure of fine protrusions and recesses of the transparent substrate.

Here, "agglomerating" refers to concentrated lumping of metal at the protrusions of the structure of fine protrusions and recesses of the substrate when the metal structure layer of fine protrusions and recesses is formed thereon. The lumps are referred to as particles.

Note that here, in the particulate structure of fine protrusions and recesses, it is desirable for the aspect ratio (length in the direction perpendicular to the substrate/length in the direction parallel to the substrate) of the protrusions (particle portions) to be 0.5 or greater. That is, it is desirable for the length of the protrusions in the direction perpendicular to the substrate to be greater than the length thereof in the direction parallel to the substrate.

The metal structure layer of fine protrusions and recesses is formed by a metal that generates localized plasmon by being irradiated with an excitation light beam. It is preferable for the metal to be gold (Au), silver (Ag), copper (Cu), aluminum (Al), platinum (Pt), or an alloy having these metals as main components. Au and Ag are particularly preferable.

The optical electrical field enhancing device of the present invention may adopt a configuration, wherein:

the transparent substrate comprises a transparent substrate main body and a transparent structure layer of fine protrusions and recesses that constitutes the structure of fine protrusions and recesses, formed by a material different from that of the transparent substrate main body.

Particularly, the transparent structure layer of fine protrusions and recesses may be formed by at least one of a metal hydroxide and a hydroxide of a metal oxide. That is, the transparent structure layer of fine protrusions and recesses may be favorably formed by a metal hydroxide, a hydroxide of a metal oxide, or a dihydroxide of a metal or a metal oxide.

It is particularly preferable for the transparent structure layer of fine protrusions and recesses to be formed by at least one of bayerite ($Al[OH]_3$) and boehmite (AlOOH). Alternatively, titanium (Ti) hydroxide or a hydroxide of titanium oxide may be employed as the material of the transparent structure layer of fine protrusions and recesses.

The transparent substrate may further comprise a second structure of fine protrusions and recesses that functions as a reflection preventing film on the back surface thereof.

In this case, the second structure of fine protrusions and recesses may be constituted by a second transparent structure layer of fine protrusions and recesses formed by a material different from that of the transparent substrate; and the second transparent structure layer of fine protrusions and recesses may be formed by at least one of a metal hydroxide and a hydroxide of a metal oxide. That is, the second transparent structure layer of fine protrusions and recesses may be favorably formed by a metal hydroxide, a hydroxide of a metal oxide, or a dihydroxide of a metal or a metal oxide.

It is particularly preferable for the second transparent structure layer of fine protrusions and recesses to be formed by at least one of bayerite ($Al[OH]_3$) and boehmite (AlOOH). The optical electrical field enhancing device of the present invention may be a sample cell, equipped with a liquid sample holding member that holds a liquid sample provided on the metal structure layer of fine protrusions and recesses of the transparent substrate.

Further, the liquid sample holding member may be a flow cell type sample cell that comprises a liquid inlet and a liquid outlet.

A measuring apparatus of the present invention comprises:

an optical electrical field enhancing device of the present invention;

an excitation light irradiating section that irradiates an excitation light beam onto the optical electrical field enhancing device; and a light detecting section that detects light generated by irradiation of the excitation light beam.

The optical electrical field enhancing device of the present invention comprises: the transparent substrate having the structure of fine protrusions and recesses on the surface thereof, and the structure layer of fine protrusions and recesses formed of metal on the structure of fine protrusions and recesses of the transparent substrate. The metal structure layer of fine protrusions and recesses has the structure of fine protrusions and recesses in which the distances among adjacent protrusions is less than the distances among adjacent protrusions corresponding thereto in the structure of fine protrusions and recesses of the transparent substrate. An enhanced optical electrical field is generated on the surface of the metal structure layer of fine protrusions and recesses by an optical electrical field enhancing effect of localized plasmon induced on the surface of the metal structure layer of fine protrusions and recesses by light irradiated onto the structure layer of fine protrusions and recesses.

The metal structure layer of fine protrusions and recesses has portions at which the distances among adjacent protrusions is less than the distances among corresponding adjacent protrusions of the structure of fine protrusions and recesses of the transparent substrate, which is a backing layer. Therefore, improvements in the optical electrical field enhancing effect by localized plasmon can be expected.

Particularly, if there are regions at which the distances among adjacent protrusions are 20 nm or less, extremely intense optical electrical field enhancing fields, called hot spots, can be generated at such regions.

Light which is generated by a test subject placed on the optical electrical field enhancing device of the present invention by light being irradiated onto the region where the test subject is placed will be enhanced by the optical electrical field enhancing effect, and the light can be detected with high sensitivity.

The optical electrical field enhancing device of the present invention employs the transparent substrate. Therefore, light (excitation light) can be irradiated from both the side of the front surface of the metal structure layer of fine protrusions and recesses and the side of the back surface of the transparent substrate. In addition, light (detected light) generated by the subject due to irradiation of the excitation light can be detected at both the side of the front surface of the metal structure layer of fine protrusions and recesses and the side of the back surface of the transparent substrate. Whether to irradiate the excitation light from and to detect the detected light at the side of the front surface of the metal structure layer of fine protrusions and recesses or the side of the back surface of the transparent substrate can be freely selected according to the type, size, etc. of the test subject in order to enable detection at higher sensitivity. That is, the degree of freedom in measurements is high, and detection at higher S/N ratios becomes possible by employing the optical electrical field enhancing device of the present invention.

In the optical electrical field enhancing device of the present invention, the structure of fine protrusions and recesses on the surface of the transparent substrate may be constituted by a transparent structure layer of fine protrusions and recesses formed of a metal hydroxide or a hydroxide of a metal oxide. In this case, the transparent structure of fine protrusions and recesses can be produced by an extremely simple production method, in which a substrate having metal vapor deposited thereon is reacted with water at high temperature. For this reason, production costs can be significantly reduced compared to conventional devices.

BEST MODE FOR CARRYING OUT THE INVENTION

Hereinafter, embodiments of the optical electrical field enhancing device of the present invention will be described with reference to the attached drawings. Note that the dimensional ratios of the constituent elements in the drawings are different from the actual dimensional ratios in order to facilitate visual understanding.

(First Embodiment)

Figure 1A:
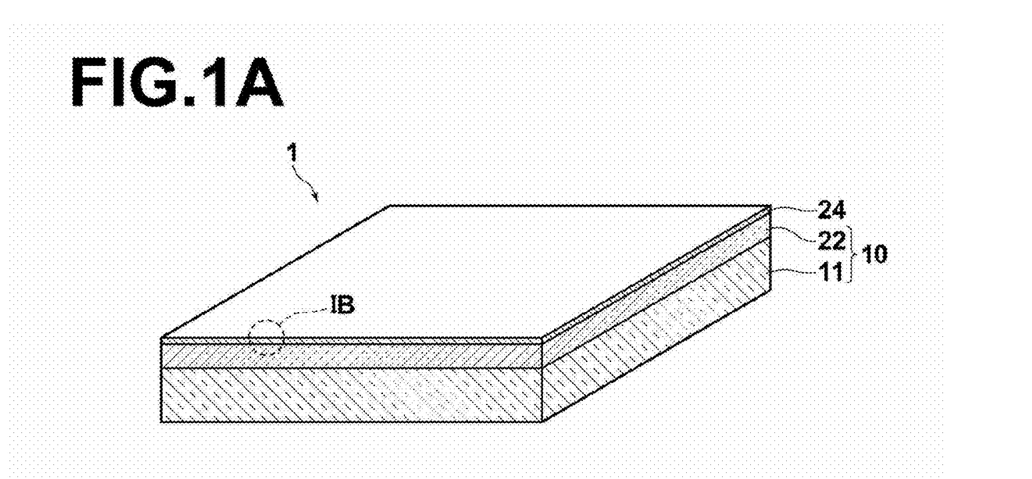
FIG. 1A is a perspective view that illustrates an optical electrical field enhancing substrate 1 as a first embodiment of an optical electrical field enhancing device.
Figure 1B:
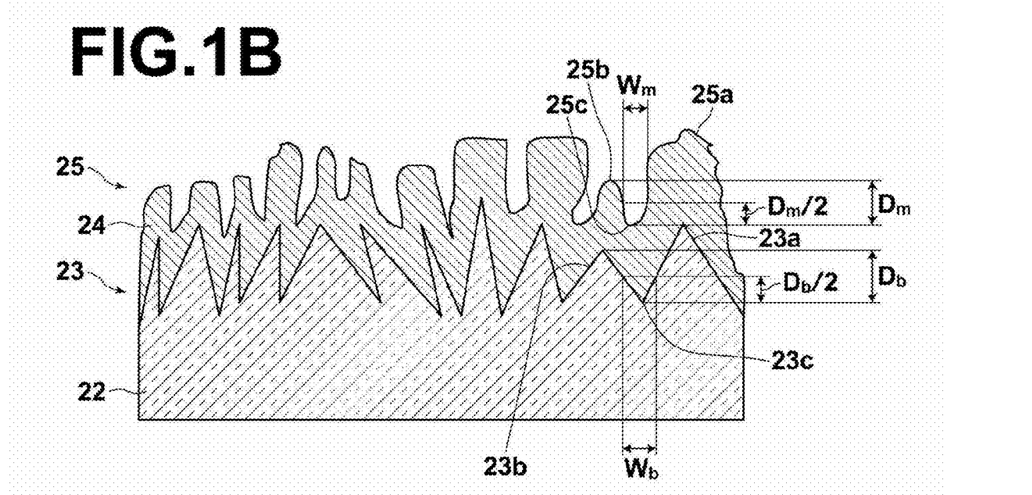
FIG. 1B is a magnified view of a portion IB of the side surface of the optical electrical field enhancing substrate 1 illustrated in FIG. 1A.

FIG. 1A is a perspective view that illustrates an optical electrical field enhancing substrate 1, which is a first embodiment of an optical electrical field enhancing device. FIG. 1B is a magnified view of a portion IB of the side surface of the optical electrical field enhancing substrate 1 illustrated in FIG. 1A.

As illustrated in FIG. 1A and FIG. 1B, the optical electrical field enhancing substrate 1 is constituted by a transparent substrate 10 having a structure of fine protrusions and recesses 23 on the surface thereof, and a metal structure layer of fine protrusions and recesses 24 formed on the surface of the structure of fine protrusions and recesses 23. Localized plasmon resonance is induced by light (hereinafter, excitation light) irradiated onto a structure of fine protrusions and recesses 25 of the metal structure layer of fine protrusions and recesses 24, and an enhanced optical electrical field is generated on the surface of the metal structure layer of fine protrusions and recesses 24 by the localized plasmon resonance.

The metal structure layer of fine protrusions and recesses 24 has a structure of fine protrusions and recesses in which the distances among adjacent protrusions is less than the distances among corresponding protrusions of the structure of fine protrusions and recesses 23 of the transparent substrate 10.

Specifically, there are portions at which the distance Wm between a protrusion 25a and an adjacent protrusion 25b in the structure of fine protrusions and recesses 25 of the metal structure layer of fine protrusions and recesses 24 is less than the distance Wb between a protrusion 23a and a protrusion 23b of the structure of fine protrusions and recesses 23 of the transparent substrate 10 corresponding to the protrusions 25a and 25b, as illustrated in FIG. 1B. Here, the distance Wm between the adjacent protrusions 25a and 25b is defined as the distance from the peak of the lower protrusion 25b to a position of the protrusion 25a having half the depth Dm/2 of the depth Dm of the deepest portion of a recess 25c between the adjacent protrusions 25a and 25b. Similarly, the distance Wb between the adjacent protrusions 23a and 23b is defined as the distance from the peak of the lower protrusion 23b to a position of the protrusion 23a having half the depth Db/2 of the depth Db of the deepest portion of a recess 23c between the adjacent protrusions 23a and 23b.

The metal structure layer of fine protrusions and recesses 24 has rounded protruding portions 24a and smaller distances among adjacent protrusions compared to a case in which a metal film is simply formed along the structure of fine protrusions and recesses 23 of the transparent substrate 10.

The structure of fine protrusions and recesses 25 of the metal structure layer of fine protrusions and recesses 24 is a structure of fine protrusions and recesses in which at least one of the length of the protrusions in the direction perpendicular to the substrate and the length of the protrusions in the direction parallel to the substrate is less than the wavelength of excitation light, such that localized plasmon can be generated on the surface of the metal structure layer of fine protrusions and recesses 24.

It is desirable for the protrusions of the metal structure layer of fine protrusions and recesses 24 to be particles formed by agglomeration of metal. It is desirable for the aspect ratio (length in the direction perpendicular to the substrate/length in the direction parallel to the substrate) of the particulate protrusions to be 0.5 or greater.

Note that it is desirable for the average depth from the peaks of the protrusions to the bottoms of recesses adjacent thereto to be 200 nm or less, and for the average pitch among the peaks of adjacent protrusions having recesses between to be 200 nm or less in the structure of fine protrusions and recesses 25 of the metal structure layer of fine protrusions and recesses 24.

Further, it is desirable for the average thickness of the metal structure layer of fine protrusions and recesses 24 to be that which efficiently generates an enhanced optical electrical field at the surface of the metal structure layer of fine protrusions and recesses opposite that of the transparent substrate by light irradiated from the side of the transparent substrate. In the case that the metal structure layer of fine protrusions and recesses is formed on the structure of fine protrusions and recesses of the substrate by vapor deposition, it is preferable for the thickness to be 400 nm or less in the case that gold is used as the metal and for the thickness to be 90 nm or less in the case that silver is used as the metal. These thicknesses do not refer to measured thickness values, but that an amount of gold or silver that forms a film having a thickness of 400 nm or less or 90 nm or less on a flat substrate is used to perform vapor deposition.

Note that it is not necessary for the distances among all adjacent protrusions in the structure of fine protrusions and recesses of the metal structure layer of fine protrusions and recesses to be less than the distances among corresponding adjacent protrusions in the structure of fine protrusions and recesses of the substrate. However, the optical electrical field enhancing effect will become more significant as the number of adjacent protrusions of the metal structure layer of fine protrusions and recesses having distances less than the distances of corresponding adjacent protrusions in the structure of fine protrusions and recesses of the substrate increases.

Particularly, if there are regions at which the distances among adjacent protrusions of the metal structure layer of fine protrusions and recesses 25 are 20 nm or less, extremely intense optical electrical field enhancing fields, called hot spots, can be generated at such regions. For this reason, it is preferable for a great number of locations at which the distance between adjacent protrusions is 20 nm or less to be present.

Note that adjacent protrusions may be in partial contact with each other.

In addition, it is preferable for the protrusions of the metal structure layer of fine protrusions and recesses 24 to be particulate protrusions that extend as particles from the surface of the structure of fine protrusions and recesses 23 of the transparent substrate 10. Surface area will increase if the protrusions are in particulate form, and therefore the amount of the test subject that adhere to the surface of the metal can be increased, resulting in an increase in detected light.

The metal material of the metal structure layer of fine protrusions and recesses 24 is a metal capable of generating localized plasmon when irradiated with excitation light. Examples of such metals include Au, Ag, Cu, Al, Pt, and alloys having these metals as their main component. Au and Ag are particularly preferable.

In the present embodiment, the transparent substrate 10 includes a transparent substrate main body 11 formed by glass or the like, and a transparent structure layer of fine protrusions and recesses 22 that constitutes the structure of fine protrusions and recesses 23 on the surface of the transparent substrate 10, formed by a material different from that of the transparent substrate main body 11. The transparent structure layer of fine protrusions and recesses is preferably a boehmite layer. Alternatively, the transparent structure layer of fine protrusions and recesses 22 may be formed by bayerite instead of boehmite. In addition, the transparent structure layer of fine protrusions and recesses 22 may be formed by a metal hydroxide or a hydroxide of a metal oxide.

The structure of fine protrusions and recesses 23 is not limited to that formed by a material different from the material of the transparent substrate main body. The structure of fine protrusions and recesses 23 may be constituted by the same material as that of the substrate main body, by processing the surface of the transparent substrate main body. For example, a glass substrate, the surface of which undergoes one of lithography, ion beam lithography, and nanoimprinting, and then undergoes a dry etching process to form a structure of fine protrusions and recesses thereon, may be employed as the transparent substrate.

Note that it is most preferable for the structure of fine protrusions and recesses 23 to be constituted by a boehmite layer 22 due to the ease with which it can be formed.

The transparent structure of fine protrusions and recesses 23 formed by the metal hydroxide or a hydroxide of a metal oxide such as boehmite has an overall saw toothed cross section, although the sizes (the sizes of the peak angles) and orientations of the protrusions vary. The transparent structure of fine protrusions and recesses 23 is that on which the metal structure layer of fine protrusions and recesses 24 can be formed, and has an average pitch and an average depth which are less than the wavelength of the excitation light. Note that here, the pitch of the transparent structure of fine protrusions and recesses 23 is the distance among the peaks of adjacent protrusions having recesses therebetween, and the depth is the distance from the peaks of the protrusions to the bottoms of the recesses adjacent thereto.

Figure 2:
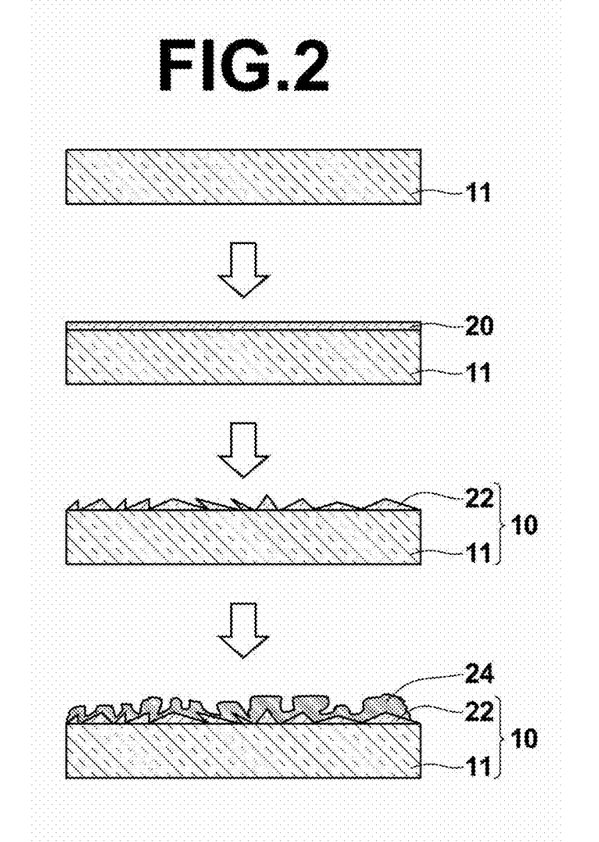
FIG. 2 is a collection of sectional diagrams that illustrate the steps of a method for producing the optical electrical field enhancing substrate.

The method by which the optical electrical field enhancing substrate 1 of the present invention is produced will be described with reference to FIG. 2.

A plank shaped transparent substrate main body 11 is prepared. The transparent substrate main body 11 is cleansed with acetone and methanol. Thereafter, an aluminum film 20 is formed on the surface of the transparent substrate main body 11 by the sputtering method.

Next, the transparent substrate main body 11 having the aluminum film 20 thereon is immersed in boiling pure water then taken out after several minutes (approximately 5 minutes). The boiling treatment (boehmite process) renders the aluminum film 20 transparent, and produces a boehmite layer 22 having a structure of fine protrusions and recesses.

Next, a metal is vapor deposited onto the boehmite layer 22, to form the metal structure layer of fine protrusions and recesses 24 on the boehmite layer.

The optical electrical field enhancing substrate 1 can be produced by the processes described above.

Figure 3A:
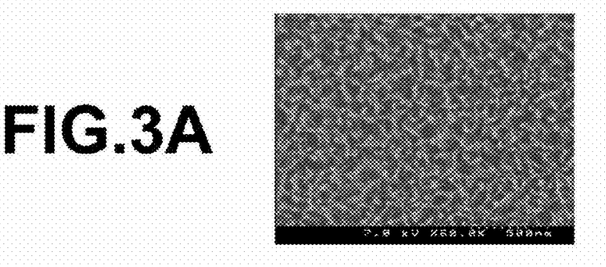
FIG. 3A is a SEM image of the surface of a boehmite layer.
Figure 3B:
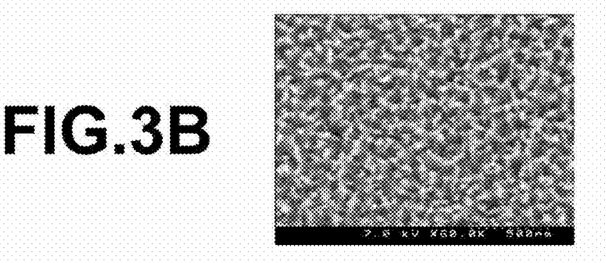
FIG. 3B is a SEM image of the surface of a (30 nm thick) metal structure layer of fine protrusions and recesses.
Figure 3C:
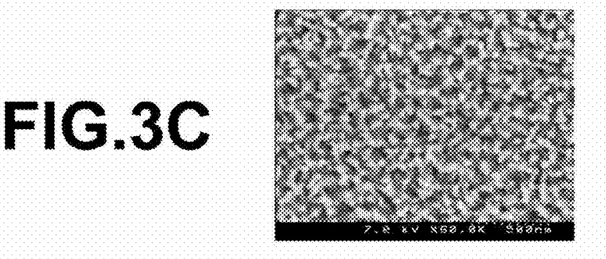
FIG. 3C is a SEM image of the surface of a (60 nm thick) metal structure layer of fine protrusions and recesses.
Figure 3D:
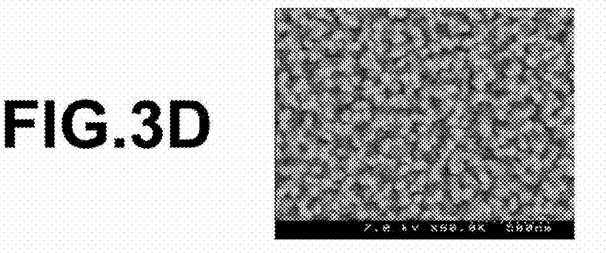
FIG. 3D is a SEM image of the surface of a (150 nm thick) metal structure layer of fine protrusions and recesses.

Note that FIG. 3A is a SEM image of the surface of a boehmite layer of a transparent substrate, the boehmite layer having been formed by sputtering aluminum at a thickness of 25 nm on a transparent substrate main body (BK-7: Eagle 2000 by Corning) then boiling for five minutes. FIGS. 3B through 3D are SEM images of the surfaces of boehmite layers on which 30 nm, 60 nm, and 150 nm worth of Au are vapor deposited respectively, obtained by a SEM (S4100 by Hitachi). Here, "30 nm, 60 nm, and 150 nm worth of Au are vapor deposited" means that amounts of Au that would become thicknesses of 30 nm, 60 nm, and 150 nm when vapor deposited onto a planar substrate are vapor deposited.

The white portions of FIGS. 3A through 3D are protrusions, and the gray portions are recesses. The patterns of protrusions and recesses are irregular, but are formed across the entirety of the surfaces of the boehmite layer, and the in plane uniformity of the structure of fine protrusions and recesses is high. It can be understood that the structure of protrusions and recesses is constituted by a great number of peak shaped protrusions from the photograph of the surface of the boehmite layer illustrated in FIG. 3A. Note that the cross section of the structure of protrusions and recesses of the boehmite layer is saw toothed as schematically illustrated in FIG. 1B. In the case that 30 nm of Au is vapor deposited, it can be seen that the protrusions of the structure of protrusions and recesses become thicker and the distances among protrusions become smaller, as illustrated in FIG. 3B. Meanwhile, the structure of fine protrusions and recesses of the metal structure layer of fine protrusions and recesses illustrated in FIG. 3B is a structure of protrusions recesses in which the peak shaped protrusions observed on the surface of the boehmite layer are substantially maintained. In addition, as the thickness of Au increases to 60 nm and 150 nm as illustrated in FIG. 3C and FIG. 3D, the protrusions are observed to become particulate in shape, the distances among the protrusions become smaller, and the structure of protrusions and recesses become different from the structure of protrusions and recesses on the surface of the boehmite layer.

Figure 3E:
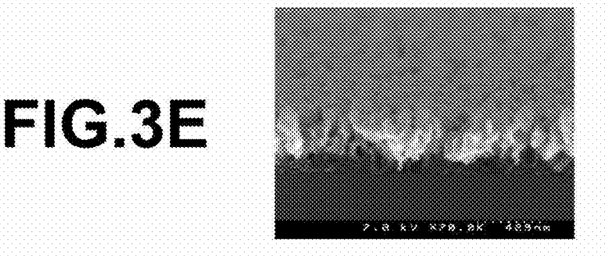
FIG. 3E is a SEM image of the cross section of a (150 nm thick) metal structure layer of fine protrusions and recesses.

FIG. 3E is a SEM image of the cross section of a metal structure layer of fine protrusions and recesses having 150 nm worth of Au vapor deposited on a boehmite layer. From the cross sectional image, it can be understood that the protrusions are in the shape of particles having large aspect ratios that extend upward from the boehmite layer, and that the metal structure of fine protrusions and recesses is a particulate fine structure having a great number of protrusions in the shape of particles. In addition, there are a great number of regions in which the distances among the particle shaped protrusions are extremely small. Note that if light is irradiated onto regions at which the distances among protrusions is approximately 20 nm or less, extremely intense optical electrical field enhancing fields called "hot spots" are generated. In addition, the amount of test subjects that become attached to the surface of the metal increases because the surface area of the protrusions increases by being formed as particles, and the amount of detected light increases correspondingly. A great number of regions in which the distances among protrusions are 20 nm or less can be formed simply, by vapor depositing 150 nm worth of metal in the manner described above.

(Second Embodiment)

Figure 4A:
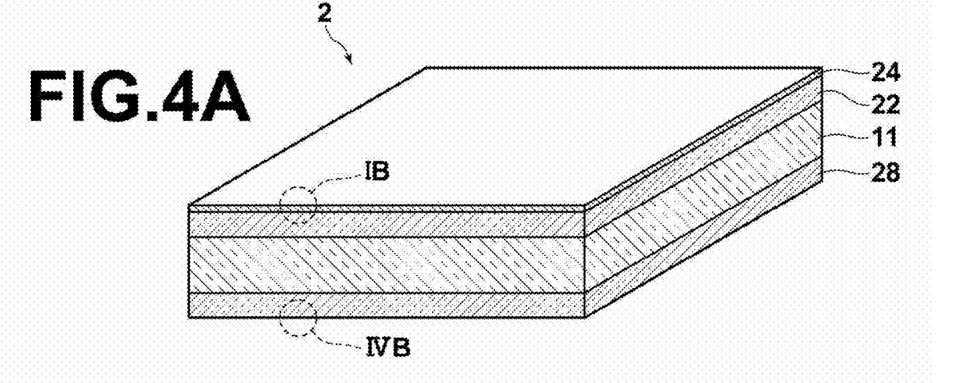
FIG. 4A is a perspective view that illustrates an optical electrical field enhancing substrate 2 as a second embodiment of an optical electrical field enhancing device.
Figure 4B:
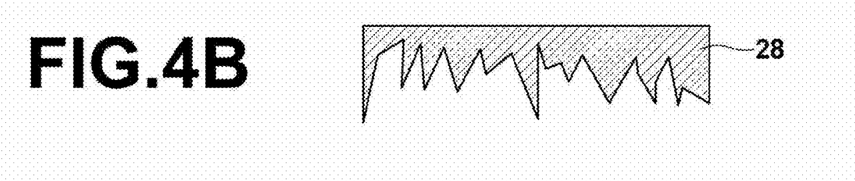
FIG. 4B is a magnified view of a portion IVB of a lower portion of the side surface of the optical electrical field enhancing substrate 2 illustrated in FIG. 4A.

An optical electrical field enhancing substrate 2, which is a second embodiment of the optical electrical field enhancing device of the present invention, will be described. FIG. 4A is a perspective view that illustrates the optical electrical field enhancing substrate 2 of the present embodiment. FIG. 4B is a magnified view of a portion IVB of a lower portion of the side surface of the optical electrical field enhancing substrate 2 illustrated in FIG. 4A.

The optical electrical field enhancing substrate 2 of the present embodiment is the optical electrical field enhancing substrate 1 of the first embodiment further equipped with a second transparent structure layer of fine protrusions and recesses 28 on the back surface thereof.

The second transparent structure layer of fine protrusions and recesses 28 is similar to the first transparent structure layer of fine protrusions and recesses 22 provided on the front surface of the transparent substrate 10, and may be constituted by a boehmite layer. The transparent structure layer of fine protrusions and recesses 28 on the back surface functions as a reflection preventing layer when light is irradiated thereon.

The optical electrical field enhancing substrate 2 of the present embodiment may be produced by forming an aluminum film not only on the front surface of the transparent substrate main body 11 but also on the back surface thereof in the method for producing the optical electrical field enhancing substrate 1 of the first embodiment, and then by administering a boiling treatment. The aluminum films on the front and back surfaces become boehmite by the boiling treatment in pure water, and similar transparent structure layers of fine protrusions and recesses 22 and 28 can be formed on both the front and back surfaces of the transparent substrate main body 11.

Figure 5:
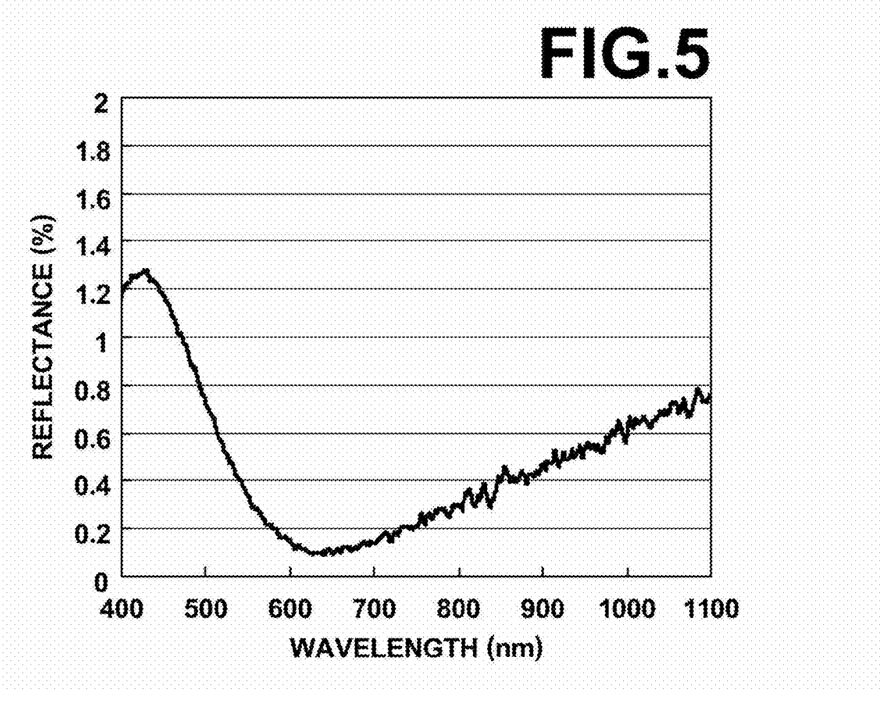
FIG. 5 is a graph that illustrates the wavelength dependent properties of the light reflectance of a boehmite layer.

Note that FIG. 5 is a graph that illustrates reflectance of a transparent substrate when light enters from a direction perpendicular to the surface of the transparent substrate (BK-7: Eagle 2000 by Corning), on which a 50 nm thick aluminum film is formed by sputtering then boiled for 5 minutes to form a boehmite layer, from the side of the boehmite layer. In the present example, a reflectance of approximately 0.1% is achieved with respect to light having wavelengths in the vicinity of 650 nm. The wavelength at which the reflectance becomes minimal can be adjusted by varying the thickness of the aluminum film which is formed by sputtering, to control interference.

(Third Embodiment)

Figure 6A:
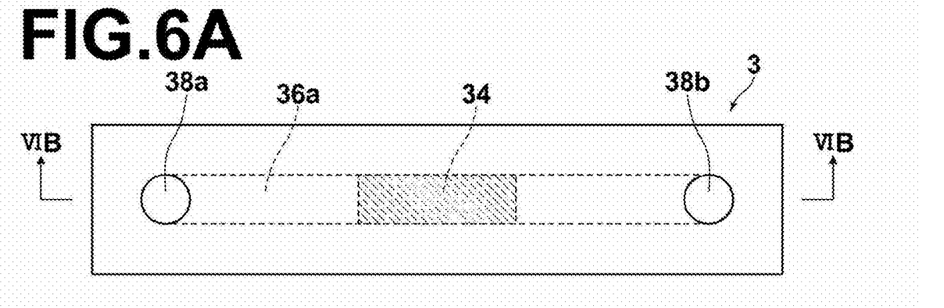
FIG. 6A is a plan view that illustrates an optical electrical field enhancing sample cell 3 as a third embodiment of an optical electrical field enhancing device.
Figure 6B:
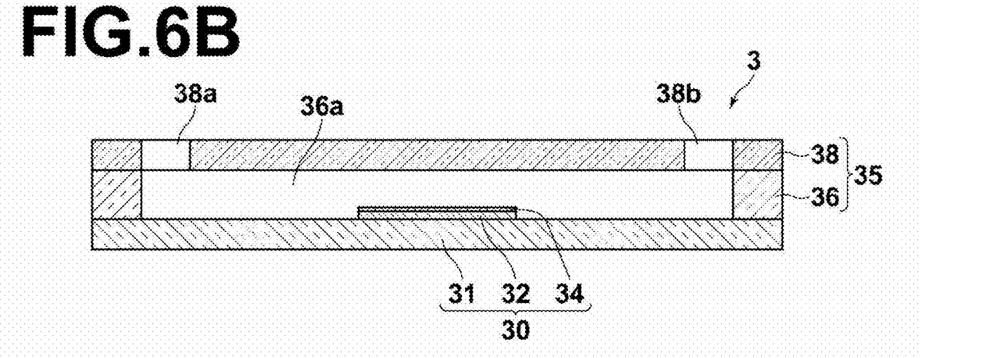
FIG. 6B is a sectional diagram of the optical electrical field enhancing sample cell 3 taken along line VIB-VIB of FIG. 6A.

A sample cell 3, which is a third embodiment of the optical electrical field enhancing device of the present invention, will be described. FIG. 6A is a plan view that illustrates an optical electrical field enhancing sample cell 3 as a third embodiment of the optical electrical field enhancing device. FIG. 6B is a sectional diagram of the optical electrical field enhancing sample cell 3 taken along line VIB-VIB of FIG. 6A.

The optical electrical field enhancing sample cell 3 of the present embodiment is equipped with: an optical electrical field enhancing substrate 30 constituted by a transparent substrate main body 31, a transparent structure layer of fine protrusions and recesses 32 provided on the surface of the transparent substrate main body 31, and a metal structure layer of fine protrusions and recesses 34 provided on the structure of fine protrusions and recesses 32; and a liquid sample holding member 35 provided on the metal structure layer of fine protrusions and recesses 34.

The optical electrical field enhancing substrate 30 has a configuration substantially similar to the optical electrical field enhancing substrate 1 of the first embodiment. That is, the transparent structure layer of fine protrusions and recesses 32 and the metal structure layer of fine protrusions and recesses 34 are similar to the transparent structure layer of fine protrusions and recesses 22 and the metal structure layer of fine protrusions and recesses 24 of the first optical electrical field enhancing device 1 illustrated in FIG. 1B, and the materials and the production methods thereof are also similar.

The liquid sample holding member 35 may be constituted by: a spacer portion 36 that holds liquid samples on the metal structure layer of fine protrusions and recesses 34 and forms a flow channel 36a for the liquid samples; and a transparent upper plate 38 such as a glass plate, equipped with an injection opening (liquid inlet) 38 through which samples are injected and a discharge opening (liquid outlet) 38b through which liquid samples which have flown through the flow channel 36a are discharged.

The optical electrical field enhancing sample cell 3 of the present embodiment can be obtained by producing the optical electrical field enhancing substrate 30 by the same method as that for producing the substrate 1 of the first embodiment, and then adhesively attaching the spacer portion 36 and the upper plate 38.

Note that the spacer portion 36 and the upper plate 38 may be integrally molded. Alternatively, the spacer portion 36 may be integrally molded with the transparent substrate main body 31.

The above embodiment was described as an optical electrical field enhancing device of the flow cell type having a flow channel equipped with a liquid inlet and a liquid outlet. Alternatively, the optical electrical field enhancing sample cell may be that which simply holds liquid samples on the metal structure layer of fine protrusions and recesses instead of a cell capable of causing liquid to flow in and out therethrough.

In addition, a second transparent structure layer of fine protrusions and recesses that functions as a reflection preventing film may be provided on the back surface of the region at which the metal structure layer of fine protrusions and recesses 34 is provided on the optical electrical field enhancing substrate 30, in the same manner as in the optical electrical field enhancing substrate 2 of the second embodiment.

The optical electrical field enhancing device of the present invention as described in the embodiments above can be favorably employed in a measuring method and a measuring apparatus that places a test subject on the metal structure layer of fine protrusions and recesses of the device, irradiates excitation light onto the location at which the test subject is placed, and detects light generated by the test subject due to irradiation of the excitation light. For example, the optical electrical field enhancing device of the present invention may be applied to an enhanced Raman spectroscopy method and a fluorescence detecting method. The optical electrical field enhancing device of the present invention may be employed as a Raman enhancing device in the enhanced Raman spectroscopy method, and may be employed as a fluorescence enhancing device in the fluorescence detecting method. In addition, light amplified by an optical electrical field enhanced by localized plasmon resonance can be detected by employing the optical electrical field enhancing device of the present invention when detecting Rayleigh scattered light, Mie scattered light, and secondary harmonic waves as well.

(Raman Spectroscopy Method and Raman Spectroscopy Apparatus)

Hereinafter, a Raman spectroscopy method and a Raman spectroscopy apparatus will be described as an example of a measuring method that employs the optical electrical field enhancing substrate 1 of the present invention.

Figure 7:
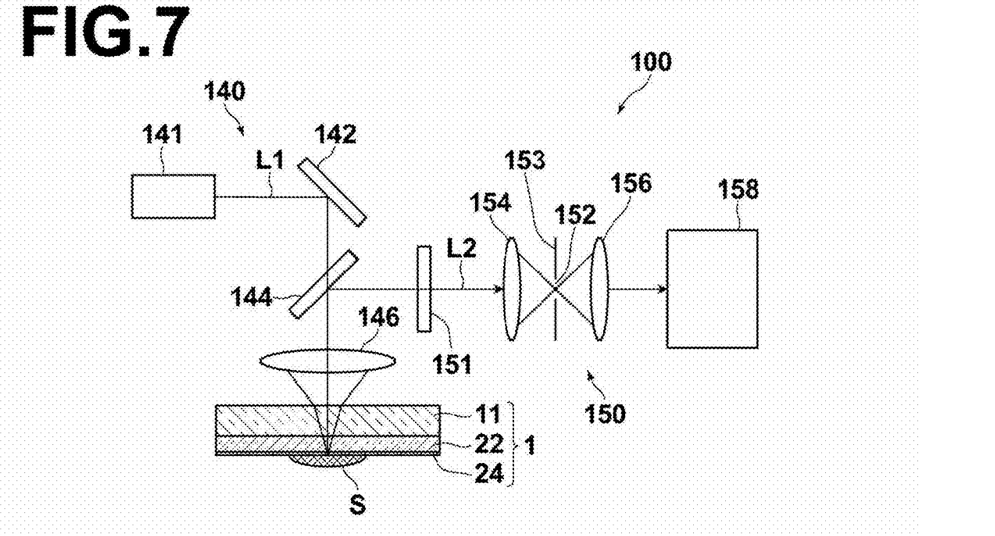
FIG. 7 is a diagram that illustrates the schematic configuration of an enhanced Raman spectroscopy apparatus equipped with the optical electrical field enhancing substrate 1.

FIG. 7 is a diagram that illustrates the schematic configuration of an enhanced Raman spectroscopy apparatus 100 equipped with the optical electrical field enhancing substrate 1.

As illustrated in FIG. 7, the Raman spectroscopy apparatus 100 is equipped with the aforementioned optical electrical field enhancing substrate 1, an excitation light irradiating section 140 that irradiates an excitation light beam L1 onto the optical electrical field enhancing substrate 1, and a light detecting section 150 that detects Raman scattered light L2, which is generated by a test subject S and is amplified by the operation of the optical electrical field enhancing substrate 1.

The excitation light irradiating section 140 is equipped with: a semiconductor laser 141 that outputs the excitation light beam L1; a mirror 142 that reflects the excitation light beam L1 output by the semiconductor laser 141 toward the optical electrical field enhancing substrate 1; a half mirror 144 that transmits the excitation light beam L1 reflected by the mirror 142 and reflects light from the side of the optical electrical field enhancing substrate 1 that includes Raman scattered light L2, which is generated by a test subject S due to irradiation of the excitation light beam L1 and is amplified, toward the light detecting section 150; and a lens 146 that focuses the excitation light beam L1 which has passed through the half mirror 144 onto a region of the optical electrical field enhancing substrate 1 at which the test subject S is placed.

The light detecting section 150 is equipped with: a notch filter 151 that absorbs the excitation light beam L1 from among light reflected by the half mirror 144 and transmits all other light; a pin hole plate 153 having a pinhole 152 that removes noise light; a lens 154 that focuses the amplified Raman scattered light L2 which has passed through the notch filter 151 into the pinhole 1521 a lens 156 that collimates the Raman scattered light which has passed through the pinhole 152; and a spectroscope 158 that detects the amplified Raman scattered light L2.

A Raman spectroscopy method that employs the Raman spectroscopy apparatus 100 to measure the Raman spectrum of a test subject S will be described.

The excitation light beam L1 is output from the semiconductor laser 141 of the light irradiating section 140. The excitation light beam L1 is reflected toward the optical electrical field enhancing substrate 1 by the mirror 142, passes through the half mirror 144, is focused by the lens 146, and is irradiated onto the optical electrical field enhancing substrate 1.

Localized plasmon is induced at the metal structure layer of fine protrusions and recesses 24 of the optical electrical field enhancing substrate 1 due to irradiation of the excitation light beam L1, and an enhanced optical electrical field is generated at the surface of the metal structure layer of fine protrusions and recesses 24. Raman scattered light L2 generated by the subject S and amplified by the enhanced optical electrical field passes through the lens 146 and is reflected toward the spectroscope 158 by the half mirror 144. Note that the excitation light beam L1 reflected by the optical electrical field enhancing substrate 1 is also reflected toward the spectroscope 158 by the half mirror 144 at this time. However, the excitation light beam L1 is cut off by the notch filter 151. Meanwhile, light having wavelengths different from that of the excitation light beam L1 passes through the notch filter 151, is focused by the lens 154, passes through the pinhole 152, is collimated by the lens 156, and enters the spectroscope 158. Note that in the Raman spectroscopy apparatus 100, Rayleigh scattered light (or Mie scattered light) has the same wavelength as the excitation light beam L1, and therefore is cut off by the notch filter, and does not enter the spectroscope 158. The Raman scattered light L2 enters the spectroscope 158, and Raman spectrum measurement is executed.

The Raman spectroscopy apparatus 100 of the present embodiment is configured to employ the optical electrical field enhancing substrate 1 of the first embodiment that effectively amplifies Raman scattered light. Therefore, highly precise Raman spectral measurement in which the reliability of data is high and data reproducibility is favorable can be executed. The surface structure of protrusions and recesses of the optical electrical field enhancing substrate 1 has high in plane uniformity. Therefore, data having favorable reproducibility can be obtained even if the light irradiation location is changed and measurement is executed for the same sample. Accordingly, it is also possible to obtain a plurality of sets of data for a single sample by changing the light irradiation location, to improve the reliability of data.

In the case that a test subject is a large sample such as a cell, amplified Raman scattered light, which is generated most intensely at the interface between the metal structure layer of fine protrusions and recesses and the test subject, is not obstructed by the test subject itself and can be detected from the side of the back surface of the transparent substrate, by adopting a configuration in which detection is performed at the back surface of the optical electrical field enhancing 1 as in the Raman spectroscopy apparatus 100 of the present embodiment. Note that the present inventors have confirmed that an metal structure layer of fine protrusions and recesses up to a certain thickness enables amplified Raman scattered light to be detected at the side of the back surface of the transparent substrate without being influenced by the metal structure layer of fine protrusions and recesses (refer to the Examples to be described below).

The Raman spectroscopy apparatus 100 of the embodiment described above is configured to cause the excitation light beam to enter the optical electrical field enhancing device 1 from the surface (back surface of the device) opposite the sample holding surface (front surface) thereof, and also to detect Raman scattered light from the back surface. Alternatively, the excitation light beam L1 may be caused to enter the surface (sample holding surface) of the metal structure layer of fine protrusions and recesses 24 and the Raman scattered light L2 may also be detected at the side of the sample holding surface as in a Raman spectroscopy apparatus 110 according to a design modification illustrated in FIG. 8.

Figure 8:
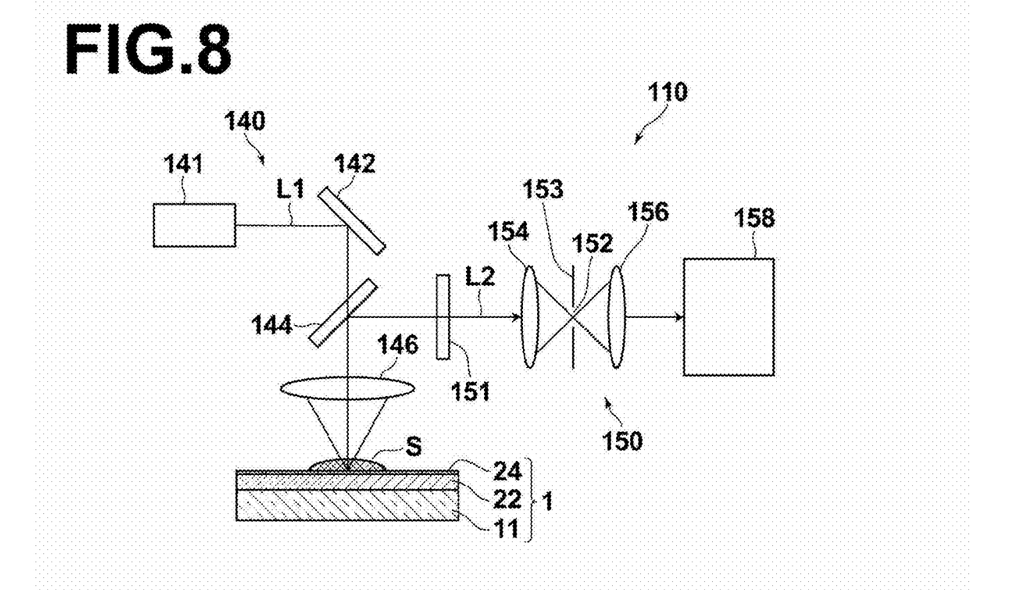
FIG. 8 is a diagram that illustrates a design modification to the enhanced Raman spectroscopy apparatus.

Further, one of the excitation light irradiating section and the light detecting section may be placed on the side of the surface of the metal structure layer of fine protrusions and recesses 24, and the other may be placed on the side of the back surface of the optical electrical field enhancing substrate 1.

As described above, the optical electrical field enhancing device of the present invention employs the transparent substrate. Therefore, light can be irradiated either from the side of the surface of the metal structure layer of fine protrusions and recesses or from the back surface of the transparent substrate. In addition, light generated by a sample due to irradiation of the light can be detected either at the side of the surface of the metal structure layer of fine protrusions and recesses or at the back surface of the transparent substrate. For this reason, whether to irradiate the excitation light from and to detect the detected light at the side of the front surface of the metal structure layer of fine protrusions and recesses or the side of the back surface of the transparent substrate can be freely selected according to the type, size, etc. of the test subject. Accordingly, the degree of freedom in measurements is high, and detection at higher S/N ratios becomes possible.

Figure 9:
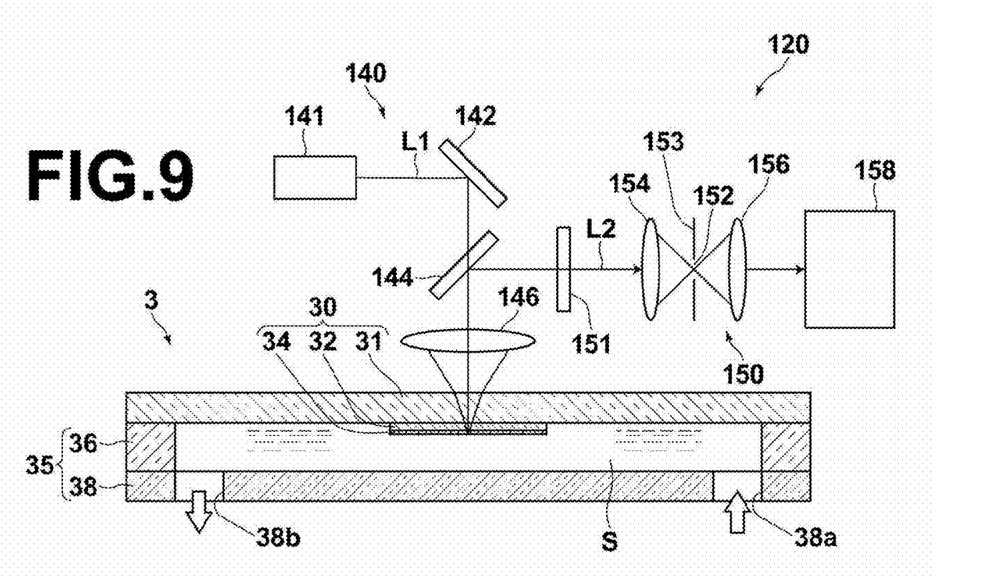
FIG. 9 is a diagram that illustrates the schematic configuration of an enhanced Raman spectroscopy apparatus equipped with the optical electrical field enhancing sample cell 3.

FIG. 9 is a diagram that illustrates the schematic configuration of a Raman spectroscopy apparatus 120 equipped with a flow cell, which is the optical electrical field enhancing device 3 of the third embodiment described above.

The Raman spectroscopy apparatus 120 illustrated in FIG. 9 differs from the Raman spectroscopy apparatus 100 illustrated in FIG. 7 in that it is equipped with the flow cell optical electrical field enhancing sample cell 3 instead of the optical electrical field enhancing substrate 1. By employing such a flow cell optical electrical field enhancing device, it becomes possible to measure the Raman spectrum of a liquid sample as a test subject while causing the liquid sample to flow.

Note that in measurements using the flow cell optical electrical field enhancing device 3 as well, the excitation light beam may be caused to enter the optical electrical field enhancing device 3 from the side of the front surface of the metal structure layer of fine protrusions and recesses, and Raman scattered light may be detected at the side of the front surface of the metal structure layer of fine protrusions and recesses. However, when measuring Raman scattered light while a liquid sample is flowing, there is a possibility that the transmissivity and the absorption rate of the liquid sample with respect to Raman scattered light will vary accompanying movement of the liquid sample. Therefore, it is preferable for Raman scattered light to be detected at side of the back surface of the substrate 30 as illustrated in FIG. 9.

As described previously, the optical electrical field enhancing device of the present invention may also be applied to a plasmon enhanced fluorescence detecting apparatus. In such a case as well, a test subject may be placed on the metal structure layer of fine protrusions and recesses of the optical electrical field enhancing device, excitation light may be irradiated from the side of the test subject, and amplified fluorescence may be detected from the side of the test subject. Alternatively, excitation light may be irradiated from the side of the back surface of the transparent substrate, and fluorescence may be detected at the side of the back surface. As a further alternative, excitation light may be irradiated from the side of the test subject, and fluorescence may be detected at the side of the back surface of the transparent substrate.

EXAMPLE 1

Hereinafter, a concrete production example of the optical electrical field enhancing substrate 1, which is the first embodiment of the optical electrical field enhancing device of the present invention, and the results of Raman spectrum measurement employing a measurement sample will be described.

[Method for Producing Optical Electrical Field Enhancing Substrate]

A glass substrate (BK-7: Eagle 2000 by Corning) was employed as the transparent substrate main body 11.

The glass substrate main body 11 underwent ultrasonic cleansing (45 kHz) with acetone for 5 minutes and with methanol for 5 minutes. Then, a 25 nm thick layer of aluminum 20 was formed on the glass substrate 11 using a sputtering apparatus (by Canon Anelva). Note that a surface shape measuring device (by TENCOR) was employed to measure the thickness of the aluminum layer, and the thickness was confirmed to be 25 nm (±10%).

Thereafter, pure water was prepared in a water bath (by Nishi Seiki K. K.) and boiled. The glass substrate main body 11 having the aluminum layer 20 thereon was immersed in the boiling water, then removed after 5 minutes had passed. At this time, it was confirmed that the aluminum became transparent 1 to 2 minutes after the glass substrate 11 having the aluminum layer 20 thereon was immersed in the boiling water. The aluminum layer 20 became the boehmite layer 22 by the boiling treatment (boehmite treatment). The results of observing the surface of the boehmite layer 22 with a SEM (S4100 by Hitachi) are the same as that illustrated in FIG. 3A.

Finally, 30 nm worth of Au was vapor deposited onto the surface of the boehmite layer 22, to produce a metal structure layer of fine protrusions and recesses (Example 1). Note that samples in which 60 nm and 150 nm worth of Au were deposited on the surface of the boehmite layer 22 (Examples 2 and 3) were also produced. The SEM image of the surface of each sample is as illustrated in FIGS. 3B through 3D, respectively.

(Measurement of Raman Scattered Light)

100 µl of an ethanol solution in which rhodamine 6G was dissolved was spotted onto each sample (Examples 1 through 3) of the optical electrical field enhancing substrate produced by the method described above. The solution was allowed to dry, and the dried samples were employed to measure Raman scattered light.

Raman scattered light was detected employing a microscopic Raman spectroscope (HR800). A laser beam having a peak wavelength of 785 nm was employed as the excitation light beam, and observation was performed at a magnification of 20×.

Figure 10:
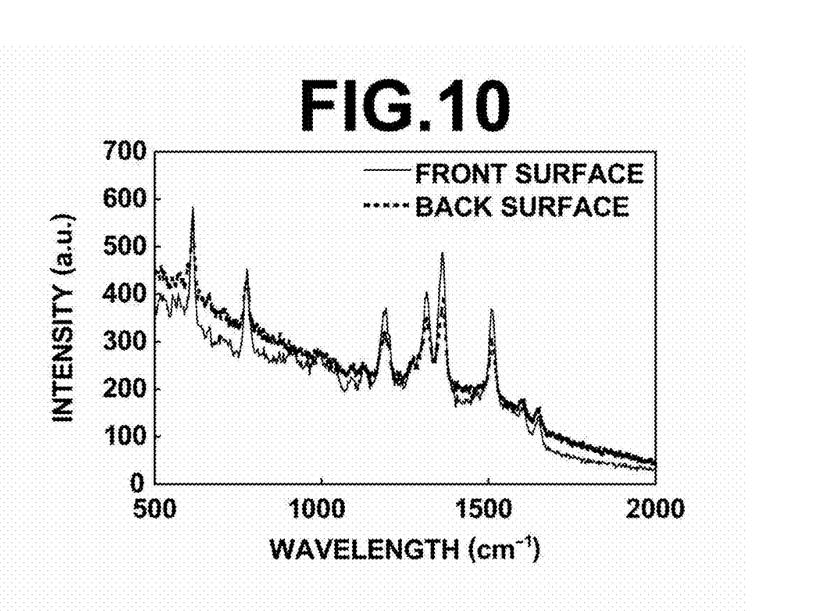
FIG. 10 is a graph that illustrates Raman spectral distributions obtained for a measured sample.

FIG. 10 is a graph that illustrates Raman shift spectrum distributions obtained by detecting Raman scattered light from the front and the back of a substrate, employing a sample (Example 2) onto which 60 nm Au is vapor deposited. Measurement from the front of the substrate refers to a case in which excitation light is irradiated from the side of the dye on the metal structure layer of fine protrusions and recesses, and Raman scattered light is detected at the side of the dye on the metal structure layer of fine protrusions and recesses. Measurement from the back of the substrate refers to a case in which excitation light is irradiated from the side of the transparent structure layer of fine protrusions and recesses under the metal structure layer of fine protrusions and recesses (excitation light is irradiated from the back surface of the substrate), and Raman scattered light is detected at the side of the back surface of the substrate.

It became clear from FIG. 10 that Raman shift signals were detected at equivalent intensities at substantially the same locations at the front and back of the substrate. In conventional Raman measurement, there were no examples in which Raman signals were detected at the side of the back surface of a substrate. However, it is clear from the Raman measurement that employs the optical electrical field enhancing device of the present invention that it is possible to detect Raman signals at the side of the back surface of the substrate.

Note that the present example employs a dye which is dried and immobilized as the test subject in the measurement sample. The thickness of the test subject is extremely small, and therefore the signal intensity at the front and back surfaces were at the same levels. However, when Raman spectroscopy is performed on a sample such as a cell having a thickness on the order of 1 µm, it is considered more advantageous to detect signals from the vicinity of the interface between the metal structure layer of fine protrusions and recesses and the sample, at which the enhancing effect is high, at the side of the back surface.

Figure 11:
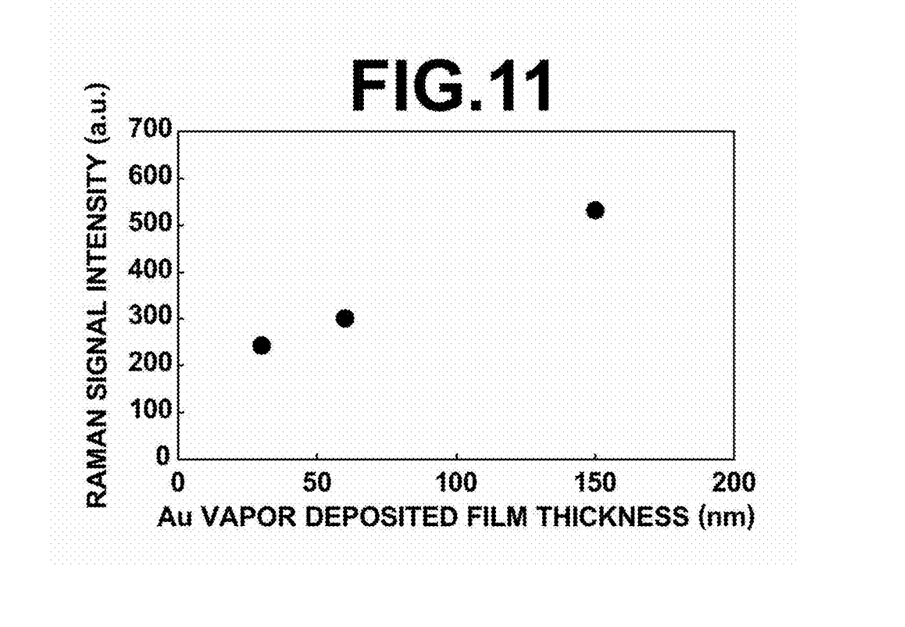
FIG. 11 is a graph that illustrates the vapor deposited Au film thickness dependent properties of Raman signal intensities obtained for a measured sample.

FIG. 11 is a graph that plots peak intensities of 1360 cm$^{-1}$ after removing white noise against Au vapor deposited film thickness as the horizontal axis, using Raman shift spectrum distributions obtained by detecting Raman scattered light at the front surfaces of the substrates for each of Examples 1 through 3.

As illustrated in FIG. 11, greater signal intensities were obtained as the Au vapor deposited film thickness became greater. As the vapor deposited film thickness of Au becomes thicker, Au forms particulate shapes as is clear from the SEM images of FIG. 3B through FIG. 3D. Further, the Au forms column shapes to increase the surface area of the metal structure of fine protrusions and recesses, and a great number of hot spots are generated due to the distances among metal protrusions becoming smaller. These are considered to be the reasons why signal intensity increased as the Au vapor deposited film thickness became greater.

What is claimed is:

1. An optical electrical field enhancing device, comprising:
   a transparent substrate having a structure of fine protrusions and recesses on the surface thereof; and
   a structure layer of fine protrusions and recesses formed of metal on the structure of fine protrusions and recesses of the transparent substrate;
   the metal structure layer of fine protrusions and recesses having a structure of fine protrusions and recesses in which the distances among adjacent protrusions is less than the distances among adjacent protrusions corresponding thereto in the structure of fine protrusions and recesses of the transparent substrate; and
   an enhanced optical electrical field being generated on the surface of the metal structure layer of fine protrusions and recesses by an optical electrical field enhancing effect of localized plasmon induced on the surface of the metal structure layer of fine protrusions and recesses by light irradiated onto the structure layer of fine protrusions and recesses.

2. An optical electrical field enhancing device as defined in claim 1, wherein:
   the structure of fine protrusions and recesses of the metal structure layer of fine protrusions and recesses is constituted by fine particulate structures, which are formed by metal that constitutes the metal structure layer of fine protrusions and recesses agglomerating on the surface of the structure of fine protrusions and recesses of the transparent substrate.

3. An optical electrical field enhancing device as defined in claim 1, wherein:
the metal that constitutes the metal structure layer of fine protrusions and recesses is one of gold, silver, copper, aluminum, and platinum.

4. An optical electrical field enhancing device as defined in claim 1, wherein:
the transparent substrate comprises a transparent substrate main body and a transparent structure layer of fine protrusions and recesses that constitutes the structure of fine protrusions and recesses, formed by a material different from that of the transparent substrate main body.

5. An optical electrical field enhancing device as defined in claim 4, wherein:
the transparent structure layer of fine protrusions and recesses is formed by at least one of a metal hydroxide and a hydroxide of a metal oxide.

6. An optical electrical field enhancing device as defined in claim 4, wherein:
the transparent structure layer of fine protrusions and recesses is formed by at least one of bayerite and boehmite.

7. An optical electrical field enhancing device as defined in claim 1, wherein:
the transparent substrate further comprises a second structure of fine protrusions and recesses that functions as a reflection preventing film on the back surface thereof.

8. An optical electrical field enhancing device as defined in claim 7, wherein:
the second structure of fine protrusions and recesses is constituted by a second transparent structure layer of fine protrusions and recesses formed by a material different from that of the transparent substrate; and
the second transparent structure layer of fine protrusions and recesses is formed by at least one of a metal hydroxide and a hydroxide of a metal oxide.

9. An optical electrical field enhancing device as defined in claim 8, wherein:
the second transparent structure layer of fine protrusions and recesses is formed by at least one of bayerite and boehmite.

10. An optical electrical field enhancing device as defined in claim 1, wherein:
a liquid sample holding member that holds a liquid sample is provided on the metal structure layer of fine protrusions and recesses of the transparent substrate.

11. An optical electrical field enhancing device as defined in claim 10, wherein:
the liquid sample holding member comprises a liquid inlet and a liquid outlet.

12. A measuring apparatus, comprising:
an optical electrical field enhancing device as defined in claim 1;
an excitation light irradiating section that irradiates an excitation light beam onto the optical electrical field enhancing device; and
a light detecting section that detects light generated by irradiation of the excitation light beam.

* * * * *